United States Patent [19]

Booth

[11] Patent Number: 5,109,880
[45] Date of Patent: May 5, 1992

[54] PORTABLE WHIRLPOOL BATHTUB CLEANER

[75] Inventor: John W. Booth, Irving, Tex.
[73] Assignee: Hydravac Corporation, Irving, Tex.
[21] Appl. No.: 663,981
[22] Filed: Feb. 18, 1991
[51] Int. Cl.$^5$ .............................................. B08B 9/06
[52] U.S. Cl. .................................. 134/108; 134/111; 134/169 C
[58] Field of Search ........... 134/105, 108, 111, 169 R, 134/169 A, 169 C; 4/490, 541, 542, 543, 544, 662

[56] References Cited

U.S. PATENT DOCUMENTS

| | | | |
|---|---|---|---|
| 4,856,125 | 8/1989 | Dijkhuizen | 134/169 C X |
| 4,857,112 | 8/1989 | Franninge | 4/541 X |
| 4,877,043 | 10/1989 | Carmichael et al. | 134/169 A X |
| 4,979,245 | 12/1990 | Gandini | 134/169 C X |

FOREIGN PATENT DOCUMENTS 0312953  4/1989  European Pat. Off. ................ 4/541

Primary Examiner—Philip R. Coe
Attorney, Agent, or Firm—Fulbright & Jaworski

[57] ABSTRACT

A portable whirlpool bathtub cleaning apparatus for cleaning and disinfecting the circulation system of the whirlpool bathtub, including a container for holding the cleaning fluid, a pump for recirculating the fluid, a plurality of hoses for attachment to the whirlpool jets, a flow line for attachment to the air intake and the suction fitting of the whirlpool bathtub. When the hoses are attached to the jets, the air intake and the suction fitting, a closed recirculating system is formed. The fluid can be heated and circulated throughout the whirlpool bathtub circulation system to clean and disinfect the whirlpool circulation system.

8 Claims, 5 Drawing Sheets

PORTABLE WHIRLPOOL BATHTUB CLEANER

FIELD OF THE INVENTION

The present invention relates to an apparatus and method for cleaning the circulation system of whirlpool bathtubs and more particularly to a portable apparatus for cleaning the circulation system of whirlpool bathtubs.

INTRODUCTION

The technology for the modern-day whirlpool bathtub was developed over thirty years ago. A major shortcoming of the whirlpool bathtub is the problem of complete drainage of the pump, plumbing lines, and multiple fittings that comprise the circulation system. The retention of water, body oil, hair, dirt, fecal matter, mineral deposits, and other bathing residues in the circulation system provides an ideal environment for the growth of fungi and bacteria. Over time this growth renders the whirlpool bathtub unsanitary. Non-portable whirlpool bathtub cleaners and related elements have been described in the Art. However, none of these systems are portable or capable of completely cleaning the complex circulation system.

U.S. Pat. No. 4,264,039 which issued to Gerald W. Moreland on Apr. 28, 1981 discloses an aerator jet for use in a spa.

U.S. Pat. No. 4,086,930 which issued to William K. Hiss on May 2, 1978 describes an automatic transmission torque converter flusher. It describes flushing devices provided with tapered plugs or ends.

U.S. Pat. No. 4,941,493 which issued to Tom Wieringa on Jul. 17, 1990 describes a device for flushing and drying the inside of a tanker truck. It shows a flushing device provided with a tapered plug.

U.S. Pat. No. 4,919,160 which issued to Joseph B. Pierce on Apr. 24, 1990 describes a system for cleaning a whirlpool bath. However, it is not a recirculating system.

U.S. Pat. No. 4,586,204 which issued to Phillip D. Daniels on May 6, 1986 describes a recirculating bathtub.

U.S. Pat. No. 4,563,781 which issued to David R. James on Jan. 14, 1986 provides an apparatus and method for a disinfecting the recirculating system of a whirlpool bathtub using a permanently attached system.

U.S. Pat. No. 4,383,341 which issued to Murray Altman on May 17, 1983 describes a bathtub self-cleaning system specifically designed for cleaning the bathtub using a spray nozzle.

U.S. Pat. No. 4,856,125 which issued to Okko K. Dijkhuizen on Aug. 15, 1989 describes a cleaning device and piping system of a whirlpool tub.

A variety of other patents including U.S. Pat. Nos. 1,240,132; 1,343,621; 3,080,265; 3,403,993; 3,493,323; 3,943,580; 3,967,323; 4,061,571; and 4,527,585 describe flushing apparatus and cleaning apparatuses for a variety of devices.

Some problems with all of the above-cited systems is that they are permanently fixed to the whirlpool bathtub and, consequently, cannot be used to clean more than one such bathtub, don't completely clean the circulation system or are not designed to work in a recirculating whirlpool system.

The present invention overcomes the foregoing problems. It provides a portable and adaptable cleaner for cleaning the circulation system of whirlpool bathtubs.

SUMMARY OF THE INVENTION

An object of the present invention is a portable whirlpool bathtub cleaner capable of cleaning several whirlpool bathtubs.

An object of the present invention is a method for cleaning whirlpool bathtubs with a portable cleaning unit.

Thus, in accomplishing the foregoing objects, there is provided in accordance with one aspect of the present invention, an apparatus for cleaning the circulation system of whirlpool bathtubs comprising a container for holding cleaning fluid, a pump attached to the container for circulating cleaning fluid through the whirlpool circulation system, a manifold attached to the pump, a plurality of suction hoses, one end of each suction attached to the manifold and the other end of each hose adapted to attach to a whirlpool jet, a flow line hose means connecting the container to the air intake and the suction fitting of the whirlpool bathtub, wherein a closed recirculating system is formed when the suction hoses are attached to the jets of the bathtub and the flow line means is attached to the air intake and the suction fitting and wherein the container, suction hoses, manifold and flow lines are packaged such that they form a portable unit.

Additional enhancements of the system can include the attachment of a filter for filtering the cleaning fluid, a heater for heating the cleaning fluid and a flow line valve to regulate the flow of the recirculating cleaning fluid.

In alternate embodiments of the invention there is included as an attachment to the suction hoses, a attachment means comprising a tube with ridges on the outside circumference of the tube, said ridged tube being covered by a tapered urethane covering. The taper is of an appropriate size so it snugly fits into a wide variety a jet diameters to form a fluid-tight seal.

In another embodiment of the present invention there is included a suction adaptor which is comprised of a suction cup which has been attached by a rod to an attachment fitting. The attachment fitting is capable of covering the suction inlet of the whirlpool. When the suction cup is attached to and positioned on the wall of the bathtub it holds the attachment fitting over the suction inlet with sufficient pressure to form a water-tight seal.

Another embodiment of the present invention is a method for cleaning and disinfecting the circulation system of a whirlpool bathtub with the portable cleaning apparatus of the present invention comprising the steps of attaching the plurality of suction hoses to each jet in the whirlpool bathtub, attaching the flow line means to the air intake and the suction fitting of the whirlpool bathtub, filling the cleaning tank with cleaning solution, heating the cleaning solution, circulating said heated cleaning solution through the whirlpool bathtub circulation system for a sufficient time to clean and disinfect the circulation system, disconnecting the portable whirlpool cleaning apparatus from the whirlpool bathtub, and circulating fresh water through the whirlpool bathtub piping system.

Other and further objects, features and advantages will be apparent from the following description of the presently preferred embodiments of the invention, given for the purpose of disclosure when taken in conjunction with the accompanying drawings.

BRIEF DESCRIPTION OF THE DRAWINGS

The invention will be more readily understood from a reading of the following specification by reference to accompanying drawings, forming a part thereof. Where examples of embodiments of the invention are shown and wherein.

DETAILED DESCRIPTION

Figure 1:
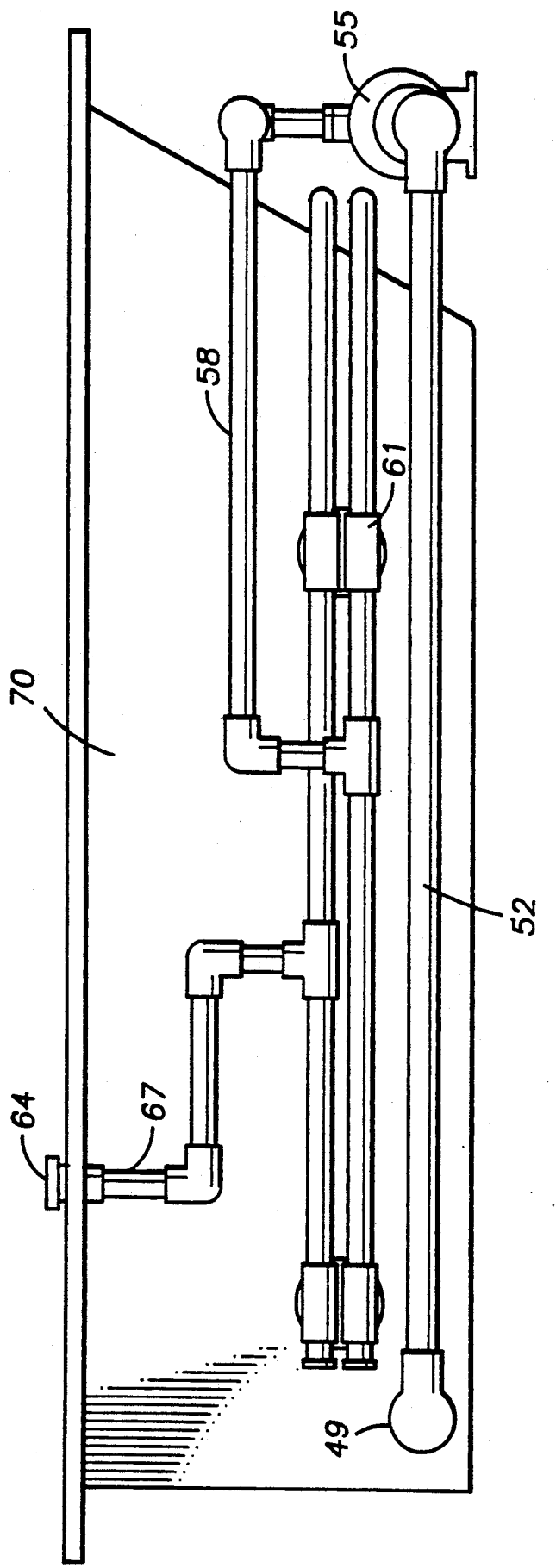
FIG. 1 is a cross section drawing of the circulation system of a whirlpool bathtub.

In the description which follows like parts are marked throughout the specifications and drawings with the same reference numerals. The drawings are not necessarily in scale and certain features of the invention may be exaggerated in scale or shown in schematic form in the interest of clarity and conciseness. It will be readily apparent to one skilled in the art that various substitutions and modifications may be made to the invention disclosed herein without departing from the scope and spirit of the invention.

Referring to the accompanying drawings, one embodiment of the present invention is an apparatus 8 for cleaning the circulation system of a whirlpool bathtub 70 comprising a container 25 for holding cleaning fluid and a pump 22 attached to said container 25 for circulating cleaning fluid throughout the whirlpool piping system. A manifold 16 is attached to the pump 22 and a plurality of suction hoses 13 are attached to the manifold. One end of each suction hose is adapted to attach to the whirlpool jet fitting 61. The system also includes a flow line means 32. The flow line hose means connects the container 25 to the air intake fitting 64 and the suction fitting 49 of the whirlpool bathtub.

In specific embodiments of the invention the flow line means further includes a flow line valve 31 for regulating the flow of the cleaning fluid and a splitter 37 for splitting the flow between the air intake fitting 64 and the suction fitting 49. The flow line means elements are connected to the apparatus 8 and whirlpool bath by the hoses 34.

A closed recirculating system is formed when the suction hoses 13 are attached to the jet fittings 61 of the whirlpool bathtub and the hoses 34 of flow line means 32 are attached to the air intake fitting 64 and the suction fitting 49.

Figure 6C:
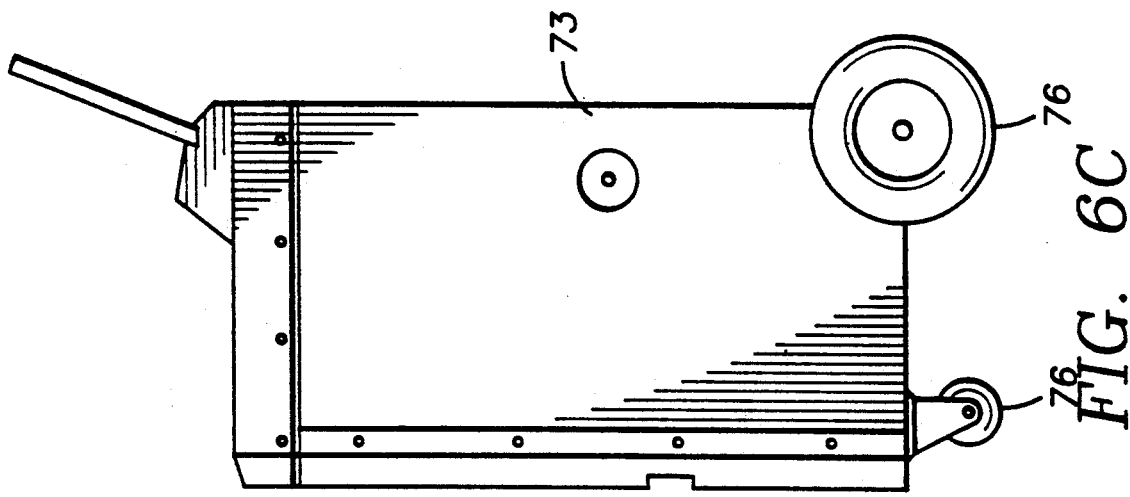
FIG. 6 shows front (A), top (B) and side (C) views of the portable cleaning unit.
Figure 6B:
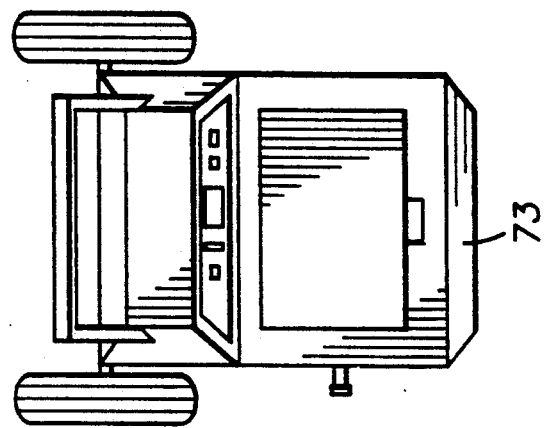
Figure 6A:
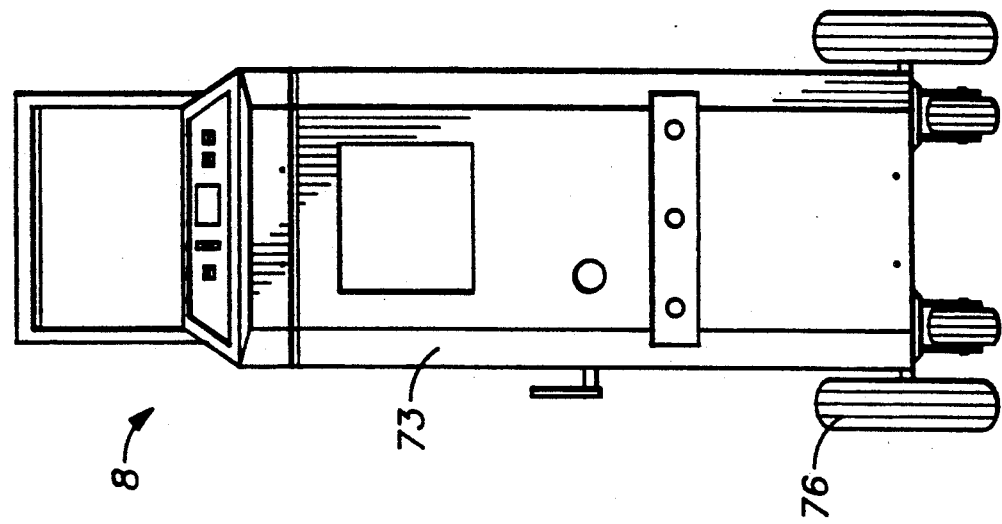

In one embodiment, the container 25, the suction hoses 13, manifold 16, flow line means 32 are all packaged such that they form a portable unit (FIG. 6). One skilled in the art will readily recognize this is only an example of packaging to make the system portable and that a variety of configurations are available to make the system portable. In this example there is a cabinet 73, holding all the elements. The manufactured apparatus includes ground fault interrupt, polarity meter, circuit breakers, switches, thermal probe, float switches to regulate fluid level and an hour meter to measure time of operation. The unit is put on mobile means 76 for ease of movement.

Figure 2:
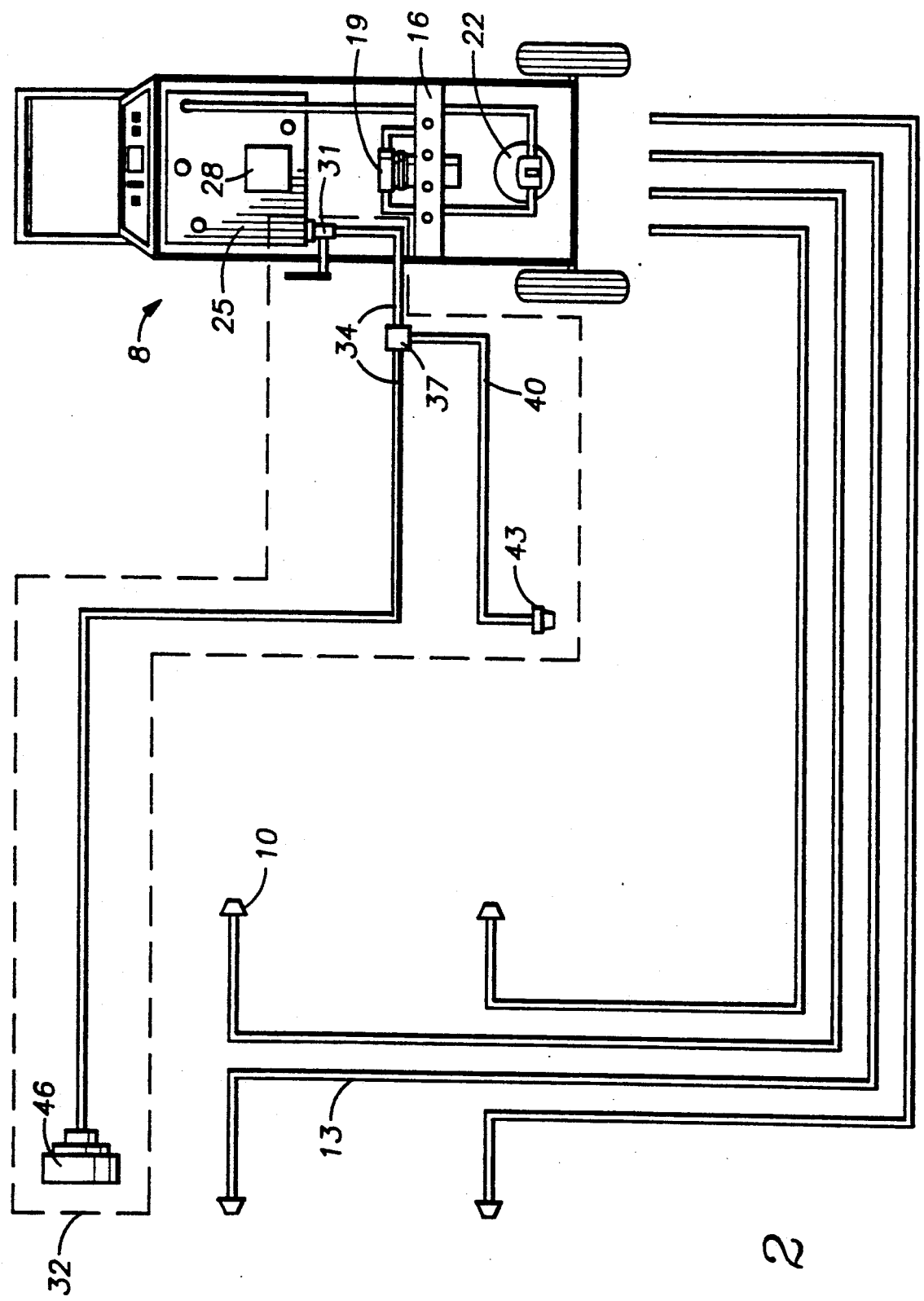
FIG. 2 is a schematic view of the portable whirlpool cleaning device.
Figure 3:
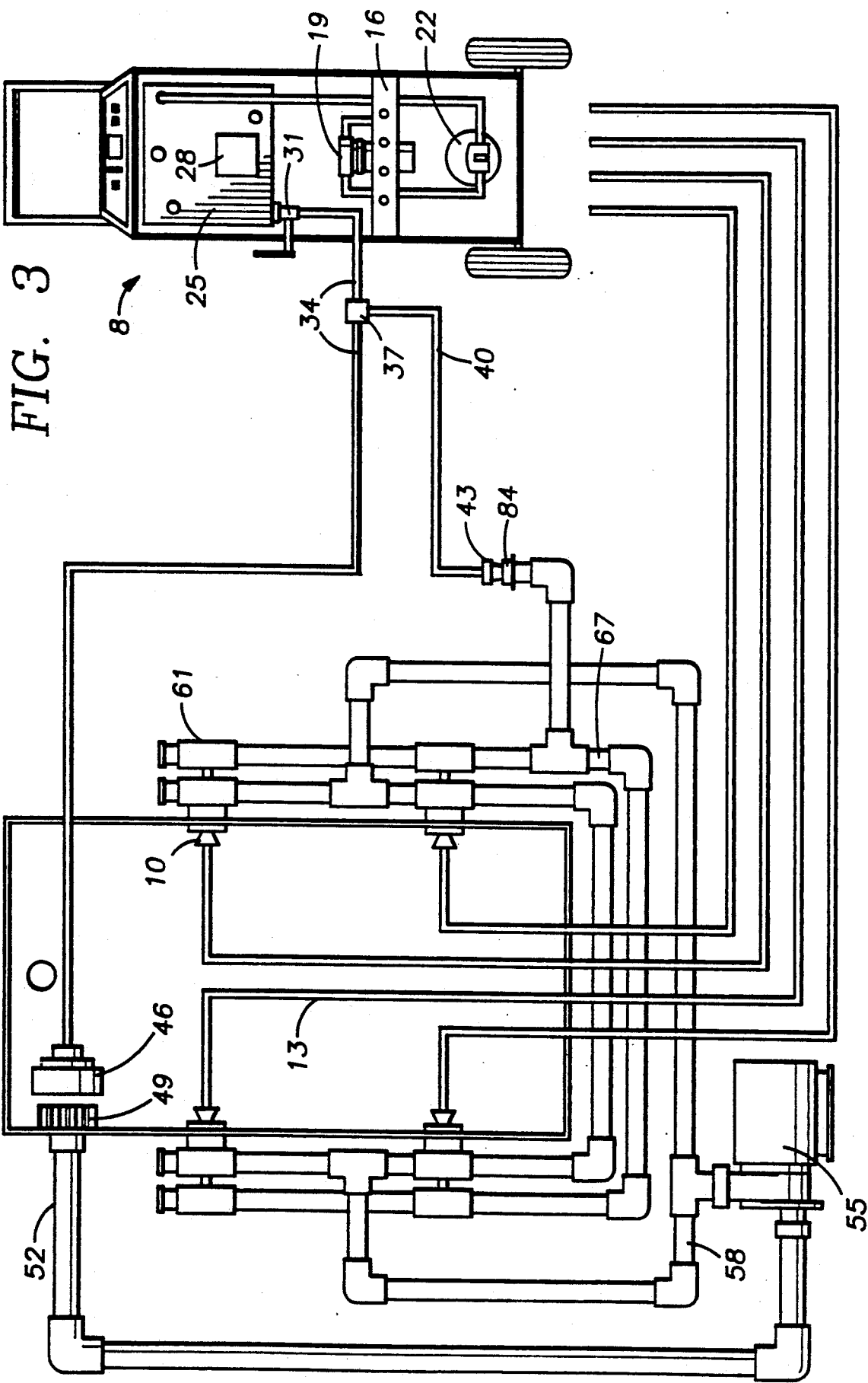
FIG. 3 is a schematic top view representation of the portable whirlpool cleaning device attached to the whirlpool bathtub.
Figure 4:
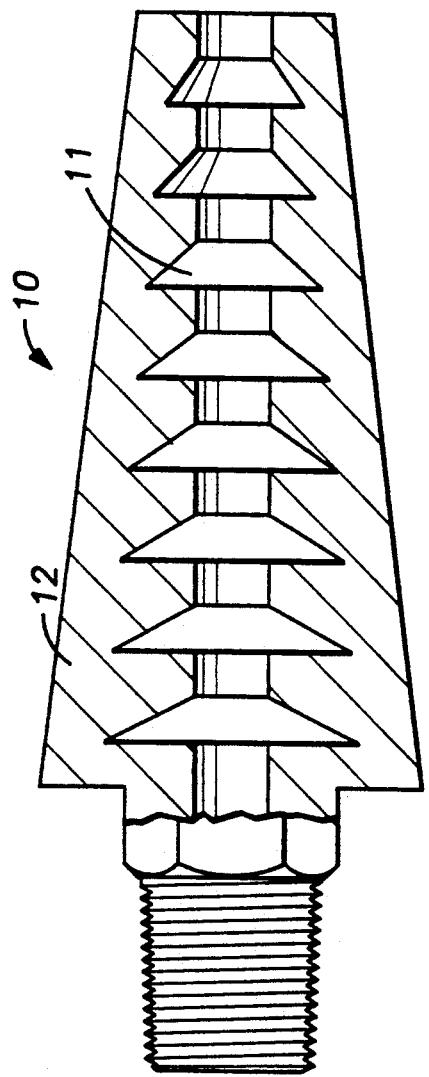
FIG. 4 is a cross section drawing of the jet attachment means.
Figure 5:
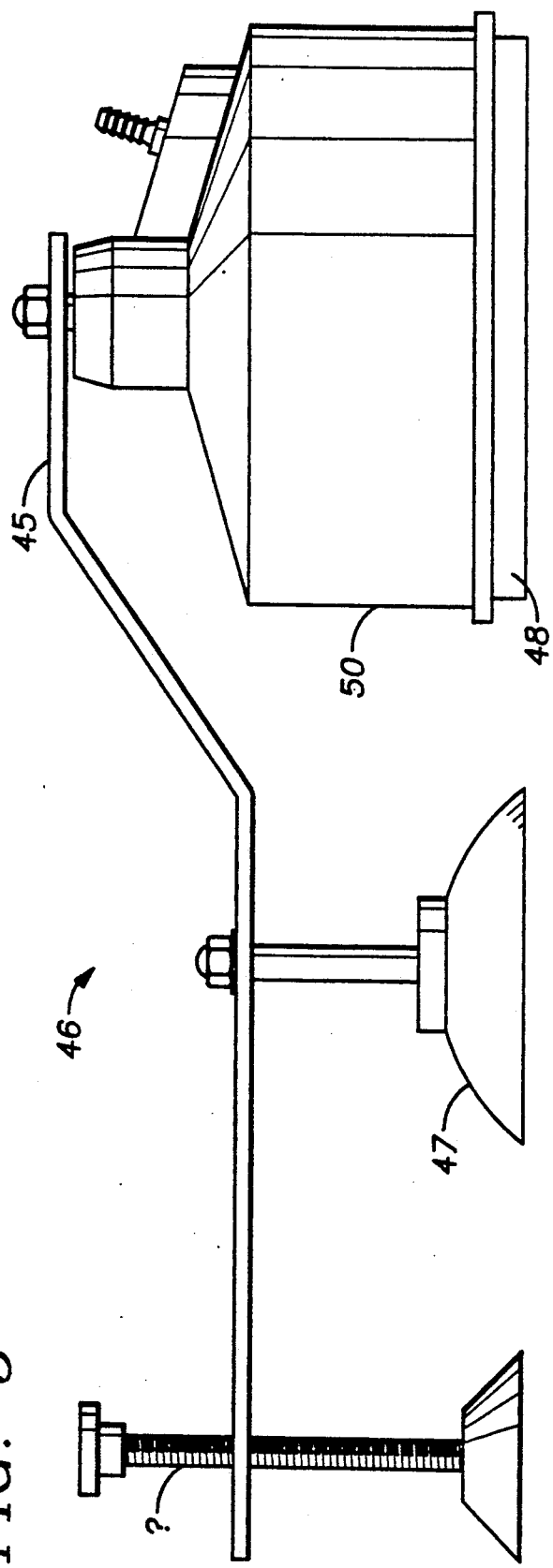
FIG. 5 is a schematic representation of the suction adaptor.

In alternate embodiments of the apparatus, there can be further included a filter 19 for filtering the cleaning fluid. This filter 19 is inserted in line with the circulating system of the cleaning apparatus 8 and can be located anywhere within the circulating system. For example, in FIG. 2 the filter 19 is between the pump 22 and the manifold 16.

In a preferred embodiment of the system there is included a heater means 28 for heating the cleaning fluid. The heating means 28 can be located in the container 25 or can be a separate unit through which the circulating fluid flows. The heater means 28 must have sufficient capacity to heat the circulating fluid to sufficient temperature to clean and disinfect the circulation system of the whirlpool bathtub. Besides the heater, the heater means will normally include a thermal probe to regulate the temperature. Further improvements include float switches to regulate the heater, depending on fluid level.

The container 25 is preferably of a sufficient size to hold sufficient cleaning fluid to fill the circulation system of the whirlpool bathtub and the circulation system of the portable cleaning apparatus.

In the preferred embodiment, the jet connector 10 is a tube insert 11. The tube insert 11 can be either metal or a hard plastic. The outside circumference of the tube insert 11 is ribbed. Covering the tube insert 11 is a tapered urethane covering 12. The tapered urethane is of sufficient size to enable the connector 10 to provide a fluid-tight seal in a wide variety of jet outlets 61 by simply pushing it into the jet outlet 61. The jet connector 10 can come in a variety of sizes and be readily attachable/detachable to the end of the suction hoses 13.

In another alternative embodiment, the suction adapter 46 is connected to the whirlpool bathtub's suction fitting 49. The suction adapter 46 fits over a variety of existing suction fittings. The suction adapter 46 is comprised of a suction cup 47. The suction cup 47 is attached to the attachment fitting 50 by a rod 45. A gasket 48 on the attachment fitting 50 seals the connection between the attachment fitting 50 and the suction fitting 49. In the preferred embodiment, an adjustment rod 44 on the suction adapter 46 is used to tighten the seal or to break the suction of the suction cup 47.

The air control connector 43 is connected to the whirlpool bathtub's air intake fitting 64. Once the air control connector 43, the suction adapter 46, and the jet connectors 10 are connected to the whirlpool bathtub, the cleaning system forms a closed loop and is ready for circulation. The tank 25 is filled with sufficient cleaning solution to accommodate the entire circulation system.

Another embodiment of the invention is a method of cleaning and disinfecting a circulating system of a whirlpool bathtub with the portable cleaning apparatus 8 of the present invention comprising the steps of attaching the plurality of suction hoses 13 to each jet 61 in the whirlpool bathtub, attaching the flow line means 32 to the air intake 64 and the suction fitting 49 of the whirlpool bathtub, filling the cleaning tank 25 with cleaning solution, heating the cleaning solution, circulating said heated cleaning solution through the whirlpool bathtub's circulation system for a sufficient time to clean and disinfect the circulation system, disconnecting the portable whirlpool cleaning apparatus 8 from the whirlpool bathtub and circulating fresh water through the whirlpool bathtub circulation system.

The pump 22 and the heating coil 28 are activated. The pump 22 causes the cleaning solution to be drawn through the whirlpool bath's circulation system. The cleaning solution is drawn through the jet connectors 10, the suction hoses 13, the manifold 16, the filter 19, and the pump 22, and enters the tank 25. The heating coil 28 heats the cleaning solution. The heated cleaning solution exits the tank 25 and travels through the flow line valve 31, the flow line 34, and to the splitter 37. The splitter 37 splits the cleaning solution. One stream travels through the suction adapter 46, the suction fitting 49, the suction piping 52, the whirlpool bathtub's circulation pump 55, the supply piping 58 and to the jet fittings 61, where it is recirculated through the portable cleaning apparatus 8. The second stream travels from the splitter 37 through the air control line 40, the air intake fitting 64, the air intake piping 67, and to the jet fittings 61, where it is recirculated through the portable cleaning apparatus 8.

The cleaning solution is recirculated through the circulation system for sufficient time to clean and disinfect the whirlpool bathtub.

Once the whirlpool bathtub has been cleaned, the pump 22 and the heating coil 28 are deactivated. The jet connectors 10, suction adapter 40, and air intake connector 43 are disconnected from the whirlpool bathtub. The whirlpool bathtub's circulation system is rinsed by filling the whirlpool bathtub with fresh water and activating the circulation pump 55 while pouring small amounts of fresh water into the air intake fitting 64.

The recirculated dirty cleaning fluid can be either flushed down the bathtub drain or removed with the portable unit for disposal at a site off premises. Because of the portability of the system, a number of whirlpool bathtubs can be cleaned by one individual in a day.

One skilled in the art will greatly appreciate that the present invention is well adapted to carry out the objects and obtain the ends and advantages mentioned, as well as those inherent therein. The devices, apparatus, methods, procedures and techniques described herein are presented representative of the preferred embodiments, are intended to be exemplary, and are not intended as limitations of the scope. Changes therein and other uses will occur to those skilled to the art which are encompassed within the spirit of the invention or defined by the scope of the appended claims.

What is claimed is:

1. An apparatus for cleaning the circulation system of a whirlpool bathtub comprising:
   a container for holding cleaning fluid;
   a pump attached to said container for circulating cleaning fluid through the whirlpool circulation system;
   a manifold attached to said pump;
   a plurality of suction hoses, one end of each suction hose attached to the manifold and the other end of each hose adapted to attach to a whirlpool jet;
   a flow line means connecting the container to an air intake and a suction fitting of the whirlpool bathtub, wherein said container, pump, manifold, suction hoses and flow line means are packaged together to form a portable unit; and
   wherein a closed recirculating system is formed when the suction hoses are attached to the jets of the bathtub and the flow line means is attached to the air intake and the suction fitting.

2. The apparatus of claim 1, further comprising a filter for filtering the cleaning fluid.

3. The apparatus of claim 1, further comprising a heater means for heating the cleaning fluid.

4. The apparatus of claim 1, wherein the suction hoses include an attachment means, said attachment means comprising a tube with ridges on the outside circumference and a tapered urethane covering said tube and ridges, said taper capable of snugly inserting into a wide variety of jet diameters forming a fluid-tight seal.

5. The apparatus of claim 1, wherein the flow line means includes a suction adapter, said adaptor comprising a suction cup attached by a rod to an attachment fitting, said attachment fitting capable of covering the suction inlet of the whirlpool system when said suction cup is attached to and positioned on the wall of the bathtub to hold the attachment fitting over the suction inlet to form a water-tight seal.

6. The apparatus of claim 5, wherein the suction adaptor further comprises an adjustment rod to adjust the tightness of the seal and to break the suction cup attachment to the bathtub.

7. The apparatus of claim 1 further comprising a flow line valve to regulate the flow of the recirculating cleaning fluid.

8. An apparatus for cleaning and disinfecting the piping system of a whirlpool bathtub comprising:
   a container for holding cleaning fluid;
   a pump attached to said container for circulating cleaning fluid through the whirlpool circulation system;
   a manifold attached to said pump;
   a plurality of suction hoses, one end of each suction hose attached to the manifold and the other end of each hose adapted to attach to a whirlpool jet;
   a flow line means connecting the container to an air intake and a suction fitting of the whirlpool bathtub, said flow line means including a flow line valve for regulating the flow of the recirculating cleaning fluid, a splitter attached to said container at one end and at the other end attached to the air intake and to the suction fitting;
   a filter attached in line between the pump and the container for filtering the cleaning fluid;
   a heater means for heating the cleaning fluid;
   an attachment means on one end of the suction hoses, said attachment means comprising a tube with ridges on the outside circumference and a tapered urethane covering said tube and ridges, said taper capable of snugly inserting over a wide variety of jet diameters to form a fluid-tight seal;
   a suction adaptor attached to the flow line, said suction adaptor comprising a suction cup attached by a rod to an attachment fitting, said attachment fitting capable of covering the suction inlet of the whirlpool bathtub, said suction cup attached to and positioned on the wall of the bathtub to hold the attachment fitting over the suction inlet to form a water-tight seal, said suction cup further including an adjustment rod to adjust the tightness of the seal and to break the suction cup attachment to the bathtub;
   wherein said container, pump, suction hoses, manifold, flow line means, filter, heater, attachment means and suction adaptor are packaged together to form a portable unit; and
   wherein a closed recirculating system is formed when the suction hoses are attached to the jets of the bathtub and the flow line means is attached to the air intake and the suction fitting.

* * * * *